(12) United States Patent
Gershon et al.

(10) Patent No.: US 10,751,268 B2
(45) Date of Patent: Aug. 25, 2020

(54) ANTI-REFLECTIVE COATING ON OXIDE PARTICLES FOR SUNSCREEN APPLICATIONS

(71) Applicant: International Business Machines Corporation, Armonk, NY (US)

(72) Inventors: Talia S. Gershon, White Plains, NY (US); Ning Li, Yorktown Heights, NY (US); Devendra Sadana, Yorktown Heights, NY (US); Teodor K. Todorov, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 23 days.

(21) Appl. No.: 15/824,288

(22) Filed: Nov. 28, 2017

(65) Prior Publication Data

US 2018/0078470 A1 Mar. 22, 2018

Related U.S. Application Data

(62) Division of application No. 15/082,639, filed on Mar. 28, 2016.
(Continued)

(51) Int. Cl.
*A61K 8/27* (2006.01)
*A61Q 17/04* (2006.01)
(Continued)

(52) U.S. Cl.
CPC .................. *A61K 8/27* (2013.01); *A61K 8/21* (2013.01); *A61K 8/25* (2013.01); *A61K 8/26* (2013.01);
(Continued)

(58) Field of Classification Search
None
See application file for complete search history.

(56) References Cited

U.S. PATENT DOCUMENTS

| 3,761,261 A | 9/1973 | Ono et al. |
| 3,863,007 A | 1/1975 | Warner, Jr. |

(Continued)

FOREIGN PATENT DOCUMENTS

| CN | 103071535 A | 5/2013 |
| CN | 104609459 A | 5/2015 |

(Continued)

OTHER PUBLICATIONS

Family Health Team, "Best Ways to Protect Your Hair From Sun Damage," Cleveland Clinic, health essentials, <https://health.clevelandclinic.org/2014/08/best-ways-to-protect-your-hair-from-sun-damage/>, published Aug. 22, 2014, p. 1-4.
(Continued)

*Primary Examiner* — Nicole P Babson
(74) *Attorney, Agent, or Firm* — Ryan, Mason & Lewis, LLP

(57) ABSTRACT

Zinc oxide compositions and methods for applying anti-reflective coating on oxide particles for sunscreen applications are provided herein. A method includes selecting two or more coating materials to be applied to zinc oxide particles in a sunscreen composition, wherein selecting is based on optical properties of the coating materials, wherein the optical properties comprises at least the refractive index of each of the coating materials, and applying the selected coating materials to the zinc oxide particles to create the sunscreen composition.

2 Claims, 2 Drawing Sheets

Related U.S. Application Data

(60) Provisional application No. 62/213,682, filed on Sep. 3, 2015.

(51) Int. Cl.

| | | |
|---|---|---|
| A61K 8/26 | (2006.01) | |
| A61K 8/29 | (2006.01) | |
| A61K 8/19 | (2006.01) | |
| A61K 8/84 | (2006.01) | |
| C09C 3/10 | (2006.01) | |
| A61K 8/81 | (2006.01) | |
| A61K 8/21 | (2006.01) | |
| A61K 8/25 | (2006.01) | |
| A61K 8/72 | (2006.01) | |
| C09C 1/04 | (2006.01) | |

(52) U.S. Cl.
CPC ............ *A61K 8/29* (2013.01); *A61K 8/72* (2013.01); *A61K 8/8123* (2013.01); *A61Q 17/04* (2013.01); *C09C 1/043* (2013.01); *C09C 3/10* (2013.01); *A61K 2800/621* (2013.01); *A61K 2800/651* (2013.01); *C01P 2004/80* (2013.01); *C01P 2004/84* (2013.01)

(56) References Cited

U.S. PATENT DOCUMENTS

| | | |
|---|---|---|
| 4,549,195 A | 10/1985 | Bluzer |
| 5,011,782 A | 4/1991 | Lamb |
| 5,028,417 A | 7/1991 | Bhat et al. |
| 5,030,699 A | 7/1991 | Hendrickson |
| 5,147,125 A | 9/1992 | Austin |
| 5,223,250 A | 6/1993 | Mitchell |
| 5,441,726 A | 8/1995 | Mitchnick |
| 5,534,056 A | 7/1996 | Kuehnle |
| 5,553,630 A | 9/1996 | Dupuis et al. |
| 5,902,569 A | 5/1999 | Oshima |
| 6,419,909 B1 | 7/2002 | Lorant |
| 6,534,044 B1 | 3/2003 | Wada |
| 6,599,355 B1 | 7/2003 | Schmidt |
| 7,143,805 B1 | 12/2006 | Weir |
| 7,241,399 B2 | 7/2007 | Haubold |
| 7,514,863 B2 | 4/2009 | Lee |
| 8,647,373 B1 | 2/2014 | Shepherd |
| 9,056,063 B2 | 6/2015 | Hanson |
| 9,144,535 B1 | 9/2015 | Daly et al. |
| 9,144,536 B1 | 9/2015 | Daly et al. |
| 9,773,931 B2 | 9/2017 | Hossain |
| 2002/0122832 A1 | 9/2002 | Hanke |
| 2003/0102099 A1 | 6/2003 | Yadav |
| 2004/0209081 A1 | 10/2004 | Hagihara |
| 2005/0008861 A1 | 1/2005 | Yadav et al. |
| 2005/0048010 A1 | 3/2005 | Kliss |
| 2005/0208005 A1 | 9/2005 | Giroud |
| 2005/0227063 A1 | 10/2005 | Lawandy |
| 2005/0238600 A1 | 10/2005 | Lien |
| 2005/0265935 A1 | 12/2005 | Hollingsworth |
| 2006/0228310 A1 | 10/2006 | Lyth |
| 2006/0241211 A1 | 10/2006 | Coughlin |
| 2006/0270053 A1 | 11/2006 | Tilak |
| 2007/0280895 A1 | 12/2007 | Weimer |
| 2008/0107695 A1 | 5/2008 | Fleissman |
| 2008/0149850 A1 | 6/2008 | Tardif et al. |
| 2008/0181920 A1 | 7/2008 | Buerger |
| 2008/0220026 A1 | 9/2008 | Maltra |
| 2009/0022765 A1 | 1/2009 | Chung et al. |
| 2009/0061001 A1 | 3/2009 | Hougaz |
| 2009/0104130 A1 | 4/2009 | Bernstein |
| 2009/0258072 A1 | 10/2009 | Schlossman |
| 2009/0258230 A1 | 10/2009 | Schlossman |
| 2010/0008872 A1 | 1/2010 | Katusic |
| 2010/0040567 A1 | 2/2010 | Katusic |
| 2010/0055138 A1 | 3/2010 | Margulies |
| 2010/0310871 A1 | 12/2010 | McCormick |
| 2011/0268678 A1 | 11/2011 | Armstrong |
| 2013/0006118 A1 | 1/2013 | Pan |
| 2013/0039858 A1 | 2/2013 | Brown |
| 2013/0216834 A1 | 8/2013 | Hashimoto |
| 2014/0142213 A1 | 5/2014 | Weiss |
| 2014/0242129 A1* | 8/2014 | Gaurav .............. A61K 8/27 |
| | | 424/401 |
| 2015/0283059 A1 | 10/2015 | Nagare |
| 2016/0082513 A1 | 3/2016 | Niedermeyer |

FOREIGN PATENT DOCUMENTS

| | | |
|---|---|---|
| EP | 1889810 A1 | 2/2008 |
| JP | 09059591 A | 3/1997 |
| JP | 2008024677 A | 2/2008 |
| JP | 2011102291 A | 5/2011 |
| WO | 2005023535 A2 | 3/2005 |
| WO | 2008017176 A2 | 2/2008 |
| WO | 2008079758 A1 | 7/2008 |
| WO | 2011004133 A2 | 1/2011 |
| WO | 2011089571 A2 | 7/2011 |
| WO | 2012046204 A1 | 4/2012 |
| WO | 2013040149 | 3/2013 |
| WO | 2013094639 A1 | 6/2013 |
| WO | 2014040177 A1 | 3/2014 |
| WO | 2014049139 A1 | 4/2014 |
| WO | 2014077189 | 5/2014 |
| WO | 2016020168 A1 | 2/2016 |

OTHER PUBLICATIONS

English language translation of WO 2013 094639 (A1) (Year: 2013).
Latha et al. "Sunscreening Agents: A Review," Journal of Clinical and Aesthetic Dermatology 6(1):16-26, 2013.
Sreejith et al. "Squaraine Dyes: A Mine of Molecular Materials," Journal of Materials Chemistry 18:264-274, 2008.
Simon Aldridge and Anthony Downs. The Group 13 Metals Aluminum, Gallium, Indium and Thallium Chemical Patterns and Peculiarities, 2011 John Wiley & Sons, Ltd., p. 623 (Year: 2011).
Merriam-Webster "Roughen." Merriam-Webster.com, Merriam-Webster, n.d. Web. Aug. 22, 2018 (Year: 2018).
Machine translation, JP 2008-024677, printer 2018.
Kelly et al. "The Optical Properties of Metal Nanoparticles: The Influence of Size, Shape and Dielectric Environment," Journal of Physical Chemistry B 107:668-677, 2003.
Garcia, "Surface Plasmons in Metallic Nanoparticles: Fundamentals and Applications," Journal of Physics D: Applied Physics 44(28), 283001, 2011.
Thokozane Moses Sithole, Synthesis and characterization of MBxOy:Eu (M = Ca, Sr, Ba) phosphors and TiO2 semiconductor for application in luminescence and energy materials, University of the Free State, Nov. 2014.
Sardar et al., Optical-absorption intensities and intermanifold emission cross sections of trivalent erbium ions in calcium fluorophosphate, Journal of Applied Physics, Sep. 2005.
Lu et al., 2008-White Up-Conversion Luminescence in Rare-Earth-Ion-Doped YAlO3 Nanocrystals, J. Phys. Chem. C 2008, 112, 15071-15074.
Refractive index of ZnO (Zinc oxide)-Bond-o, http://refractiveindex.info/?shelf=main&book=ZnO&page=Bond-o, Mar. 25, 2016.
Refractive index of SiO2 (Silicon dioxide, Silica, Quartz)—Malitson, http://refractiveindexinfo/?shelf=main&book=SiO2&page=Malitson, Mar. 25, 2016.
Schubert et al., Design of multilayer antireflection coatings made from co-sputtered and low-refractive-index materials by genetic algorithm. Optics Express vol. 16, No. 8, 2008.
Law et al., ZnO—Al2O3 and ZnO—TiO2 Core-Shell Nanowire Dye-Sensitized Solar Cells. J. Phys. Chem. B 2006, 110, 22652-22663.
Pu et al., Core/shell structured ZnO/SiO2 nanoparticles: Preparation, characterization and photocatalytic property. Applied Surface Science 257 (2010) 393-397.

(56) References Cited

OTHER PUBLICATIONS

Mantz et al., Progress in Organic Coatings 47 (2003) 432-442, "A multiple-scattering model analysis of zinc oxide pigment for spacecraft thermal control coatings.".

Song et al., Toxicology Letters 199 (2010) 389-397, "Role of the dissolved zinc io and reactive oxygen species in cytotoxicity of ZnO nanoparticles.".

Bohren et al., "Absorption and Scattering of Light by Small Particles", Wiley-VCH,© 2004, Weinheim.

Bae et al., J. Phys. Chem. B 2005, 109, 2526-2531, "Comparative Structure and Optical Properties of Ga-, In-, and Sn-Doped ZnO Nanowires Synthesized by thermal evaporation.".

NanoComposix, Silver Nanoparticles: Optical Properties, http://nanocomposix.com/pages/silver-nanoparticles-optical-properties, Apr. 20, 2016.

Awazu et al., 2007-A Plasmonic Photocatalyst Consisting of Silver Nanoparticles Embedded in Titanium Dioxide, J. AM. CHEM. SOC. 2008, 130, 1676-1680.

Sherry et al., Localized Surface Plasmon Resonance Spectroscopy of Single Silver Nanocubes, Nano Lett., vol. 5, No. 10, 2005.

Aguirre et al., Ag@ZnO Core_Shell Nanoparticles Formed by the Timely Reduction of Ag+Ions and Zinc Acetate Hydrolysis in N,N-Dimethylformamide: Mechanism of Growth and Photocatalytic Properties, J. Phys. Chem. C 2011, 115, 24967-24974.

Haynes et al., Nanosphere Lithography: Tunable Localized Surface Plasmon Resonance Spectra of Silver Nanoparticles, J. Phys. Chem. B 2000, 104, 10549-10556.

J. Nobbmann, "FAQ: How important are refractive index & adsorption for nanoparticles?" http://www.materials-talks.com/blog/2014/08/05/faq-how-important-are-refractive-index-absorption-for-nanoparticles/ Materials Talks, Aug. 5, 2014, p. 1-2.

Tsuzuki et al., Nanoparticle Coatings for UV Protective Textiles, RJTA vol. 14 No. 2 2010.

Li et al., Transparent and Light-Emitting Epoxy Super-Nanocomposites Containing ZnO-QDs/SiO2 Nanocomposite Particles as Encapsulating Materials for Solid-State Lighting, J. Phys. Chem. C 2008, 112, 18616-18622.

Li et al., 2011-Sol-gel preparation and characterization of nanoporous ZnO_SiO2 coatings with broadband antireflection properties, Applied Surface Science 257 (2011) 9752-9756.

Messaoudi et al., "Synthesis and characterization of ZnO/Cu2O core-shell nanowires grown by two-step electrodeposition method." Applied Surface Science 343 (2015) 148-152.

Luo et al., Facile synthesis of composition-tuned ZnO/ZnxCd1-xSe nanowires for photovoltaic applications, Nanoscale Research Letters (2015) 10:181.

List of IBM Patents or Applications Treated as Related.

Cuprous Oxide, Chemical Book, pp. 1-4, Accessed Sep. 18, 2017, https://www.chemicalbook.com/ProductChemicalPropertiesCB9853041_EN.htm.

Machine translation WO 2011/004133, printed 2017.

Wikipedia "Band Gap" last modified Jul. 18, 2017, https://en.wikipedia.org/wiki/Band_gap.

Machine translation WO 2012/046204, printed 2017.

Faure, B. et al. Dispersion and Surface Functionalization of Oxide Nanoparticles for Transparent Photocatalytic and UV-protecting Coatings and Sunscreens, Sci Technol. Adv. Mater. 14 2013, 023001.

Ultraviolet Radiation and the INTERSUN Programme [online]. WHO, Nov. 2003 [retrieved on Jun. 8, 2017]. Retrieved from the internet <http://www.who.int/uv/uv_and_health/en/>.

Smijs et al. Titanium Dioxide and Zinc Oxide Nanoparticles in Sunscreens: Focus on Their Safety and Effectiveness, Nanotechnology, Science and Applications 4:95-112, Oct. 2011.

Wikipedia, List of Refractive Indices, last modified Feb. 15, 2017; https://en.wikipedia.org/wiki/List_of_refractive_indices.

Naylor et al. "Sunscreens," accessed 2017, http://telemedicine.org/sundam/sundam2.4.2.html.

Definitions of "incorporate" from Merriam-Webster, Vocabulary.com. Downloaded from https://www.merriam-webster.com/dictionary/incorporate adn https://www.vocabulary.com/dictionary/incorporate respectively May 11, 2017.

Synonyms of "incorporate" downloaded from http://www.thesaurus.com/browse/incorporate on May 11, 2017.

Tariq Jan, et al. Sn Doping Induced Enhancement in the Activity of ZnO Nanostructures against Antibiotic Resistant S. Aureus Bacteria; Int J Nanomedicine. vol. 8, pp. 3679-3687; Published online Sep 30, 2013.

Bhatti, et al. Optical Properties of Chromium & Cobalt Doped Zinc Oxide Powder Prepared by Sol-Gel Combustion Method, with the Assistance of Microwave Radiations; International Journal of Advanced Tech. in Engineering and Science; vol. 3, issue 10; pp. 80-85; published Oct. 2015.

\* cited by examiner

FIG. 3

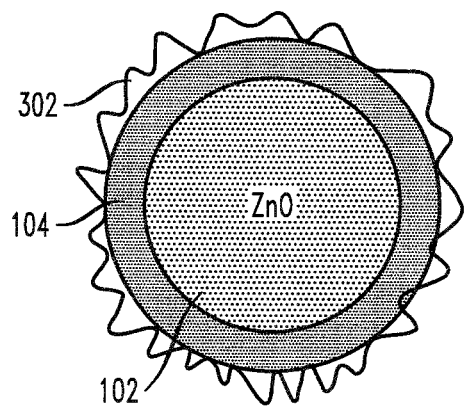

FIG. 4

| SELECT ONE OR MORE COATING MATERIALS TO BE APPLIED TO ONE OR MORE ZINC OXIDE PARTICLES IN A SUNSCREEN COMPOSITION, WHEREIN SAID SELECTING IS BASED ON ONE OR MORE OPTICAL PROPERTIES OF EACH OF THE COATING MATERIALS, WHEREIN THE ONE OR MORE OPTICAL PROPERTIES COMPRISES AT LEAST THE REFRACTIVE INDEX OF EACH OF THE COATING MATERIALS | 402 |
|---|---|
| APPLY THE ONE OR MORE SELECTED COATING MATERIALS TO THE ONE OR MORE ZINC OXIDE PARTICLES TO CREATE THE SUNSCREEN COMPOSITION | 404 |

ANTI-REFLECTIVE COATING ON OXIDE PARTICLES FOR SUNSCREEN APPLICATIONS

FIELD

The present application generally relates to chemical technology, and, more particularly, to sunscreen technologies.

BACKGROUND

Sunscreen creams and other such compositions are commonly used to prevent ultraviolet (UV) radiation (also referred to herein as "light" in this context) from reaching the skin of a human user and causing damage. It is noted that UV light is an electromagnetic radiation with a wavelength range between approximately 280 nanometers (nm) and approximately 400 nanometers (specifically, that is the range of UV radiation that is not absorbed by the ozone).

A common active ingredient of existing sunscreen compositions is zinc oxide (ZnO). ZnO is a semiconductor that has a specific band gap, and particles of ZnO used in existing sunscreen compositions are typically approximately 50-200 nm in size. Additionally, in existing sunscreen compositions, typical ZnO materials are capable of absorbing UV light (that is, blocking the UV light from passing through the sunscreen composition to be absorbed by the skin of the user) within a wavelength range of approximately 290 nm through only approximately 350-380 nm.

Additionally, high sun protection factor (SPF) sunscreen compositions, which can absorb a large majority of the UV light in the range of 290-380 nm, require the addition of a higher density of ZnO particles, which causes the composition to become white and/or opaque due to light scattering from the ZnO particles, and which is an often undesirable property to consumers.

SUMMARY

In one embodiment of the present invention, zinc oxide compositions and methods for applying anti-reflective coating on oxide particles for sunscreen applications are provided. An exemplary method can include steps of selecting two or more coating materials to be applied to one or more zinc oxide particles in a sunscreen composition, wherein said selecting is based on one or more optical properties of each of the coating materials, wherein the one or more optical properties comprises at least the refractive index of each of the coating materials, and applying the one or more selected coating materials to the one or more zinc oxide particles to create the sunscreen composition.

In another embodiment of the invention, a composition can include multiple zinc oxide particles suspended within a medium forming sunscreen composition, and one or more coating materials applied to each of the multiple zinc oxide particles, wherein each of the coating materials has a refractive index that is between the refractive index of air and the refractive index of zinc oxide, and wherein at least one of the coating materials incorporates a textured surface.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 3 is a diagram illustrating a roughened surface coating of a ZnO particle, according to an exemplary embodiment of the invention; and FIG. 4 is a flow diagram illustrating techniques, according to an embodiment of the invention.

DETAILED DESCRIPTION

As described herein, an embodiment of the present invention includes zinc oxide compositions, methods of fabrications thereof and methods of use thereof. Specifically, at least one embodiment of the invention includes one or more anti-reflective coatings (ARC) on oxide particles for sunscreen applications.

As further detailed herein, one or more embodiments of the invention include generating ZnO compositions and methods of use thereof for effectively blocking more and/or all of the complete spectrum of UV light (that is, as noted above, the UV radiation that is not absorbed by the ozone, and which ranges between approximately 280 nm and 400 nm) while also preventing whitening effects caused by the scattering of light in the visible spectrum (that is, radiation between approximately 400 nm and 700 nm). As used herein, "scattering" refers to the deflection of rays of visible light from their original path due to interaction with particle surfaces.

Figure 1:
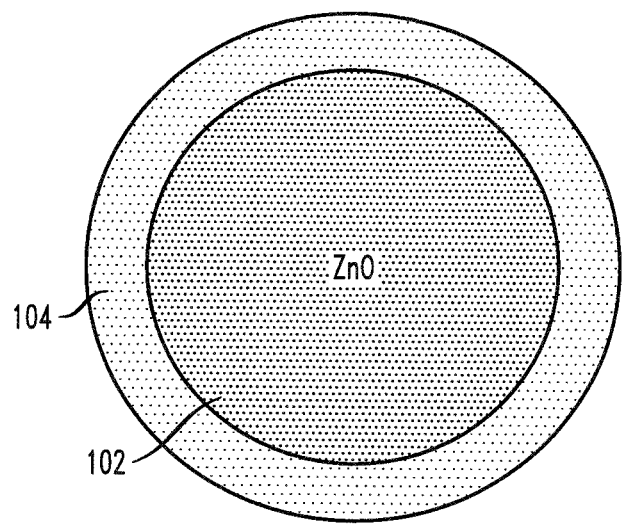
FIG. 1 is a diagram illustrating coating of a ZnO particle, according to an exemplary embodiment of the invention.

As noted above, at least one embodiment of the invention includes applying an ARC to the outside of ZnO particles (within a sunscreen composition) to create a core-shell structure. FIG. 1 is a diagram illustrating coating of a ZnO particle, according to an exemplary embodiment of the invention. By way of illustration, FIG. 1 depicts a single-layer ARC 104 applied to the outside of the ZnO particle 102. In such an example embodiment, the ARC 104 can be a material having a refractive index that is between that of air and ZnO, which allows light to better couple into the ZnO particle 102 and prevents scattering at the ZnO/air interface. In one or more embodiments of the invention, examples of ARC materials can include silicon dioxide ($SiO_2$), magnesium fluoride ($MgF_2$), one or more fluoropolymers, aluminum oxide ($Al_2O_3$), zinc sulfide (ZnS), titanium dioxide ($TiO_2$), or one of more combinations thereof. The selection of the particular composition of ARC material(s) can depend, for example, on the specific properties desired (by a user) from the coating.

Additionally, and as further detailed herein, in at least one embodiment of the invention, the coating(s) applied to a ZnO particle can be dense or porous. As used herein, a "dense" coating refers to a coating that is solid and contains no voids, whereas a "porous" coating refers to a coating that contains voids which may become filled with air. Further, in at least one embodiment of the invention, the coating(s) applied to a ZnO particle can include surface texturing or can lack surface texturing.

A coating, such as utilized in one or more embodiments of the invention, can increase the light that can enter a ZnO particle, thereby increasing the UV absorption of the particle assembly. For example, at least one embodiment of the invention includes applying one or more ARC materials to a ZnO particle to implement and/or manipulate a refractive index grading to manage the ZnO particle's interaction with light (via, for example, absorption and scattering).

As also described herein, an optical ARC which surrounds a ZnO (or, in one or more embodiments of the invention, TiO$_2$) particle present in a sunscreen composition reduces the scattering of light from the particle surface. The reduction of scattering can reduce the whitening of the sunscreen for a given level of UV protection. In at least one embodiment of the invention, implementing a coating that suppresses the scattering of visible light by the (ZnO) particles can consequently allow more of the UV light to be transmitted through the sunscreen layer, as opposed to being deflecting at the (ZnO) particle surface. By transmitting the visible light instead of scattering it, the (ZnO) particles will have a decreased whitening effect (which would likely be a desirable product characteristic).

In one or more embodiments of the invention, such as depicted in FIG. 1, the coating can include a single layer. Additionally, and as depicted in FIG. 2, at least one embodiment of the invention can include applying multiple layers of coating, wherein the refractive index of the layers can be graded between that of the ZnO and that of the ambient environment (for example, air).

Figure 2:
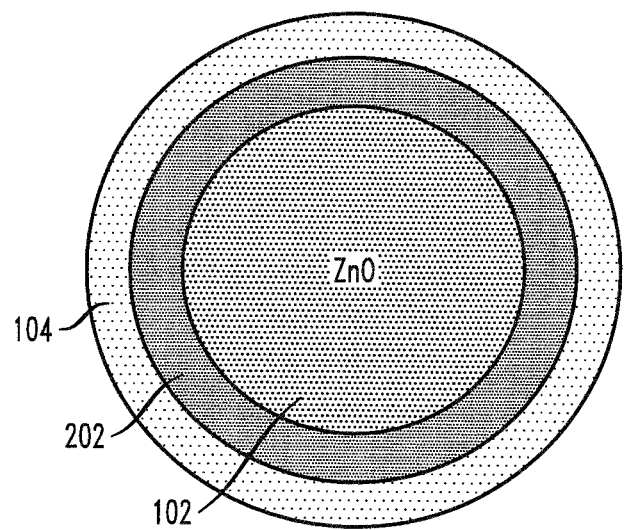
FIG. 2 is a diagram illustrating a multi-layer coating of a ZnO particle, according to an exemplary embodiment of the invention.

Accordingly, FIG. 2 is a diagram illustrating a multi-layer coating of a ZnO particle 102, according to an exemplary embodiment of the invention. By way of illustration, FIG. 2 depicts a coating that utilizes multiple layers in an ARC stack, namely layer 202 and layer 104. In such an embodiment of the invention, the multiple layers (202 and 104) in the ARC stack can vary in refractive index from between that of ZnO and that of an ambient environment (for example, air) in gradations. Additionally, in one or more embodiments of the invention, a coating can include two or more materials that are combined in a given layer to achieve a specific refractive index.

FIG. 3 is a diagram illustrating a roughened surface coating of a ZnO particle 102, according to an exemplary embodiment of the invention. By way of illustration, FIG. 3 depicts a coating 104 which incorporates a textured surface 302 to enhance light in-coupling into the ZnO particle 102. Roughening the surface of a coating can, by way of example, facilitate the transition from air to the ZnO particle (that is, n=2). In other words, in one or more embodiments of the invention, a roughened surface can be designed and implemented to perform similarly to a coating with an infinitely graded refractive index. Additionally, one or more embodiments of the invention can include incorporating a roughened and/or textured surface on a coating layer with or without adding/applying a second coating layer.

FIG. 4 is a flow diagram illustrating techniques, according to an embodiment of the present invention. Step 402 includes selecting one or more coating materials to be applied to one or more zinc oxide particles in a sunscreen composition, wherein said selecting is based on one or more optical properties of each of the coating materials, wherein the one or more optical properties comprises at least the refractive index of each of the coating materials. The refractive index of each of the one or more selected coating materials has a refractive index that is between the refractive index of air and the refractive index of zinc oxide. Additionally, the optical properties can include reduction of scattering at an interface of air and the one or more zinc oxide particles.

As described herein, in one or more embodiments of the invention, the one or more coating materials can include silicon dioxide, magnesium fluoride, one or more fluoropolymers, zinc sulfide, aluminum oxide, titanium dioxide, or one or more combination thereof. Also, the one or more coating materials can include two or more coating materials, wherein the two or more coating materials vary in refractive index. In one or more embodiments of the invention, the two or more coating materials can be applied to the one or more zinc oxide particles in distinct layers via a gradation based on refractive index. Further, in at least one embodiment of the invention, the two or more coating materials can be combined to form a single combined coating material having a target refractive index.

Step 404 includes applying the one or more selected coating materials to the one or more zinc oxide particles to create the sunscreen composition. The techniques depicted in FIG. 4 can also include texturing the surface of the one or more coating materials. Additionally, at least one embodiment of the invention can also include applying an additional one or more coating materials to the textured surface of the one or more coating materials.

Also, an additional embodiment of the invention includes a composition that includes multiple zinc oxide particles suspended within a medium forming sunscreen composition, and one or more coating materials applied to each of the multiple zinc oxide particles, wherein each of the coating materials has a refractive index that is between the refractive index of air and the refractive index of zinc oxide, and wherein at least one of the coating materials incorporates a textured surface. In such a composition, the one or more coating materials can include at least one of (i) silicon dioxide, (ii) magnesium fluoride, (iii) one or more fluoropolymers, (iv) aluminum oxide, (v) zinc sulfide, (vi) titanium dioxide, and (vii) one of more combinations thereof. Additionally, in such a composition, the one or more coating materials can incorporate a textured surface, and the one or more coating materials can include two or more coating materials that vary in refractive index.

Additionally, in one or more embodiments of the invention, the two or more coating materials can be applied to the one or more zinc oxide particles in distinct layers via a gradation based on refractive index. Alternatively, in one or more embodiments of the invention, the two or more coating materials can be combined to form a single combined coating material having a target refractive index.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, applying a coating to a ZnO particle, whereby the coating increases the light that can enter the ZnO particle, thereby increasing the UV absorption of the particle assembly.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:

applying a first coating layer to the outside of each of one or more zinc oxide particles, wherein the first coating layer consists of a combination of silicon dioxide, magnesium fluoride, multiple fluoropolymers, aluminum oxide, and zinc sulfide; and applying a second coating layer to the outside of the first coating layer on each of one or more zinc oxide particles, wherein the second coating layer consists of a combination of silicon dioxide, multiple fluoropolymers, aluminum oxide, and zinc sulfide.

2. The method of claim 1, comprising:

texturing the surface of the first coating layer.

* * * * *